(12) United States Patent
Komalarajun et al.

(10) Patent No.: US 9,127,213 B2
(45) Date of Patent: Sep. 8, 2015

(54) METHOD FOR PREDICTING CATALYST PERFORMANCE

(75) Inventors: Varut Komalarajun, San Ramon, CA (US); Cesar Ovalles, Walnut Creek, CA (US); Estrella Rogel, Orinda, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 700 days.

(21) Appl. No.: 13/294,865

(22) Filed: Nov. 11, 2011

(65) Prior Publication Data

US 2013/0118951 A1    May 16, 2013

(51) Int. Cl.
| | |
|---|---|
| C10G 99/00 | (2006.01) |
| G01N 30/02 | (2006.01) |
| C10G 21/00 | (2006.01) |
| G01N 30/00 | (2006.01) |
| G01N 30/88 | (2006.01) |

(52) U.S. Cl.
CPC ........ *C10G 21/003* (2013.01); *G01N 2030/009* (2013.01); *G01N 2030/8854* (2013.01)

(58) Field of Classification Search
CPC . C10G 2300/206; G01N 30/02; G01N 33/28; G01N 33/2823
USPC ............... 208/14, 45, 309; 73/61.56, 61.59
See application file for complete search history.

(56) References Cited

U.S. PATENT DOCUMENTS

| | | | |
|---|---|---|---|
| 4,493,765 A | 1/1985 | Long et al. | |
| 4,628,204 A | 12/1986 | Maes | |
| 4,865,740 A | 9/1989 | Nolte et al. | |
| 4,865,741 A | 9/1989 | Nolte et al. | |
| 4,988,446 A | 1/1991 | Haberman et al. | |
| 4,990,773 A | 2/1991 | Supernaw et al. | |
| 5,092,983 A | 3/1992 | Eppig et al. | |
| 5,574,215 A | 11/1996 | Bunger et al. | |

(Continued)

FOREIGN PATENT DOCUMENTS

| | | |
|---|---|---|
| EP | 400989 | 5/1990 |
| WO | 00/77120 A2 | 12/2000 |

(Continued)

OTHER PUBLICATIONS

Izquierdo, A. Carbogani L., Leon, V. Parisi, A., Fuel Sci. Tech. Int. 7, 561 (1989).

(Continued)

*Primary Examiner* — Ellen McAvoy
(74) *Attorney, Agent, or Firm* — Frank C. Turner; Richard J. Schulte; Michael E. Carmen (57) ABSTRACT

Disclosed herein is a method involving the steps of: (a) precipitating an amount of polyaromatic compounds from a liquid sample of a first hydrocarbon-containing feedstock having solvated polyaromatic compounds therein with one or more first solvents in a column; (b) determining one or more solubility characteristics of the precipitated polyaromatic compounds; (c) analyzing the one or more solubility characteristics of the precipitated polyaromatic compounds; and (d) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the hydrocarbon-containing feedstock.

20 Claims, 4 Drawing Sheets

(56) References Cited

U.S. PATENT DOCUMENTS

| | | | |
|---|---|---|---|
| 5,861,228 | A | 1/1999 | Descales et al. |
| 5,969,237 | A | 10/1999 | Jones et al. |
| 6,773,921 | B1 | 8/2004 | Schabron et al. |
| 7,790,646 | B2 * | 9/2010 | Lopez et al. ............. 502/21 |
| 7,875,464 | B2 † | 1/2011 | Schabron |
| 8,658,030 | B2 * | 2/2014 | Osaheni et al. ........... 208/324 |
| 2003/0211621 | A1 | 11/2003 | Rovani et al. |
| 2011/0062058 | A1 | 3/2011 | Roger et al. |
| 2011/0664412 | | 3/2011 | Roger et al. |
| 2011/0198264 | A1 * | 8/2011 | Tanaka et al. ............ 208/19 |
| 2013/0067991 | A1 * | 3/2013 | Schabron et al. ......... 73/23.37 |
| 2013/0124106 | A1 * | 5/2013 | Rogel et al. ............. 702/25 |
| 2014/0020456 | A1 * | 1/2014 | Dreyfus et al. .......... 73/61.59 |
| 2014/0021101 | A1 * | 1/2014 | Schabron et al. ......... 208/309 |

FOREIGN PATENT DOCUMENTS

| | | |
|---|---|---|
| WO | 00/77120 A3 | 12/2000 |
| WO | 02/063292 A1 | 8/2002 |
| WO | 03/096011 A1 | 11/2003 |
| WO | 2011/032123 | 3/2011 |
| WO | 2011/032125 | 3/2011 |
| WO | 2011/113017 | 9/2011 |

OTHER PUBLICATIONS

Gray, M. R., Jokuty, P., Yeniova, H., Nazarewycz, L., Wanke, S. E., Achia, U., Krzywicki, A., Sanford, E. C., Sy, O. K. Y., Can. J. Chem. Eng. 69, 833 (1991).

Reynolds, J., Symposium on Correlation between Resid Characterization and Processability, presented before the Division of Petroleum Chemistry, American Chemical Society, Dallas, Apr. 9-14 (1989).

Shi, T-P, Xu, Z-M, Cheng, M., Hu, Y-X, Wang, R-A Energy & Fuels 13, 871 (1999) 6)Strausz, O. P., Mojelsky, T. W., Lown, E. M., Fuel, 71, 1355 (1992).

Gauthier, T., Quoineaud, A-A, Merdrignac, I., Energy & Fuels, 20, 2028 (2006).

LePage, J. F.; Morel, F.; Trassard, A. M.; Bousquet, J. Prepr. Papers Am. Chem. Soc., Div. Pet. Chem., 23, 470 (1987).

Rogel, E., Carbognana, L., presented at the 1999 SPE Latin American and Caribbean Petroleum Engineering Conference held in Caracas, Venezuela, Apr. 21-23, (1999).

Layrisse, I, Rivas, H., Acevedo, S., Rev. Tec. Intevep, 4, 3-18 (1984).

Nomura et al. Energy & Fuels, 13, 287 (1999).

Storm, D. A., Edwards, J. C., DeCanio, S. J., Sheu, E. Y., Energy & Fuels, 8, 561 (1994).

Murray, M. R. "Upgrading Petroleum Residues and Heavy Oil", Dekker, New York, (1994) and references therein.

Chung, K. H., Xu, C., Gray, M., Zhao, Y., Kotlyar, Sparks, B., Rev. Proc. Chem. Eng., 1, 41 (1998). b) Zhao, S., Sparks, B. D., Kotltar, L. S., Chung, K. H., Catal. Today, 125, 122 (2007) and references therein.

Speight, J. G., "The Chemistry and Technology of Petroleum", 3er Ed., New York, Dekker p. 442 (1998) and references therein.

Michael, G., Al-Siri, M., Khan, Z. H., A. Ali, F. A., Energy & Fuels, 19, 1598 (2005).

Boduszynski, M. M., Robbers, J. A., Chevron Document No. 8790158, Feb. 1987.

Boduszynski, M. M., Chevron Document No. CP9945530, Feb. 1987.

Clay, R. J., Boduszynski, M. M., Hubert, J. M., Chevron Document No. 879185, Dec. 1987.

Schabron, J. F.; Rovani, J. F., Fuel 87, 2008, 165.

Barton, A. F. M. Handbook of Solubility Parameters and Other Cohesion Parameters; CRC Pres Inc.: Boca Raton, FL, 1983 pp. 93.

Gray. M.R., Energy and Fuels, 17, 9. 1566 (2003).

Barton, A. F. M., Handbook of Solubility Parameters and other Cohesion Parameters, CRC Press, USA, 1991, p. 63.

Cortell, Jessica M. et al, "Influence of Vine Vigor on Grape (Vitisvinifera L. Cv. Pinot Noir) Anthocyanins. 2. Anthocyanins and Pigmented Polymers in Wine," J. Agric. Food Chem., 55, pp. 6585-6595 (2007).

Aske, Narve et al., "Determination of Saturate, Aromatic, Resin, and Asphaltenic (SARA) Components in Crude Oils by Means of Infrared and Near-Infrared Spectroscopy", Energy & Fuels, 15, pp. 1304-1312 (2001).

Boduszynski, M. M. et al, "Composition of heavy petroleums: I. Molecular weight, hydrogen deficiency, and heteroatom concentration as a function of atmospheric equivalent boiling point up to 1400° F.", Energy & Fuels, 1, pp. 2-11 (1987).

Corbett, L. W., "Composition of Asphalt Based on Generic Fractionation11111111111, Using Solvent Deasphaltening, Elution-Adsorption Chromatography, and Densimetric Characterization," Analytical Chemistry, p. 576.

Snyder, L.R., "Principles of Adsorption Chromatography", Marcel Dekker, Inc. New York, pp. 206-210.

Schabron, J. F. et al, "Initial studies using ultrasonic spectroscopy for monitoring changes in residua with pyrolysis", Fuel 85, pp. 2093-2105 (2006).

Chiantore, Oscar and Simonelli, Alessandra, "Precipitation-redissolution Liquid Chromatography of Styrene-ethyl Acrylate Copolymerskk", Polymer Engineering and Science, 39(8), pp. 1383-1388 (1999).

Boduszynski, M. M. et al, "Separation of Solvent-Refined Coal into Solvent-Derived Fractions", Analytical Chemistry, 54, pp. 372-375 (1982).

Burrell, H. "Solubility Parameters." Interchemical Review, pp. 3-16 (1955).

Carrier, H. et al, "Acoustic method for measuring asphaltene flocculation in crude oils", Journal of Petroleum Science and Engineering, pp. 11-117.

Schabron, J. F. et al, "Coking indexes using the Heithaus titration and asphaltene solubility", Preprints—American Chemical Society, Division of Petroleum Chemistry, 44(2), pp. 187-189 (1999).

Schabron, J. F. et al, "The Solubility and Three-Dimensional Structure of Asphaltenes", Petroleum Science and Technology, 16 (3-4), pp. 361-376 (1998).

Schabron, J. F. et al, "Petroleum Residua Solubility Parameter/Polarity Map: Stability Studies of Residua Pyrolysis," Department of Energy Report under contract # DE-FC26-98FT40322 Task pp. 1, 2, 24, (1999).

Schabron, J. F. et al, Molecular Weight/Polarity Map for Residua Pyrolysis, Fuel, 80(4), pp. 529-537.

Schabron, J. F. et al, "Non-Pyrolytic Heat Induced Deposition from Heavy Oils", Fuel, 80(7), p. 919-928 (2001).

Schabron, J. F. et al, "Residua Coke Formation Predictability Maps", Fuel 81,(17), pp. 2227-2240.

Schabron, J. F. et al, "Predicting Coke Formation Tendencies", Fuel 80(10) pp. 1435-1446 (2001).

Schabron, J. F. et al, "Characterization of Residua During Pyrolysis", Preprints, Div. of Petroleum Chemistry, American Chemical Society, 47(1), pp. 17-21 (2002).

Schabron, J. F. et al, "The Characterization of Petroleum Residua", U. S. Department of Energy under contract # DE-FC21-86MC110761, 68 pages (1993).

Schabron, J. F. et al, "Thermal Analysis for Monitoring Incipient Coke Formation", U. S. Department of Energy under contract # DE/FG36/01G011018, 18 pages (2002).

Schabron, J. F. et al, "Coke Formation Process Model for Petroleum Refining Efficiency Improvement", U. S. Department of Energy under contract # DE/FG36/01G011018, 40 pages (2002).

Singh, I. D et al., "Characteristic Changes of Asphaltenes During Visbreaking of North Gujarat Short Residue", Fuel, 69 (3), pp. 289-292 (1990).

Small, P.A., "Some Factors Affecting the Solubility of Polymers", Journal of Applied Chemistry, pp. 71-80 (1953).

"Standard Test Method for Separation of Asphalt into Four Fractions 1", ASTM International, Designation D4124-09.

"Standard Test Method n-Heptane Insulbles 1", Designation: D 3279-97 (Reapproved 2001).

(56) References Cited

OTHER PUBLICATIONS

"Energy and Environmental Profile of the US Petroleum Refining Industry", Prepared by Energetics Inc., for U.S. Department of Energy Office of Industrial Technologies (1988).

Schabron, J. F. et al, "Asphaltene Determinator Method for Automated On-Column Precipitation and Redissolution of Pericondensed Aromatic Asphaltene Components", Energy Fuels, (24), pp. 5984-5996, DOI: 10.102/ef100822f (2010).

Fan, T. et al., "Rapid and Accurate SARA Analysis of Medium Gravity Crude Oils", Energy & Fuels (16), pp. 1571-1575 (2002).

Schabron, J. F. et al, "On-column precipitation and re-dissolution of asphaltenes in petroleum residua", Fuel 87, pp. 165-176, (2008).

Grizzle, Patrick L., et al., "Automated Liquid Chromatographic Compound Class Grou-Type Separation of Crude Oils and Bitumens Using Chemically Bonded Aminosilane", Anal. Chem. (58), pp. 2389-2396 ((1986).

Jewell, D. M. et al., "Ion-Exchange, Coordination, and Adsorption Chromatographic Separation of Heavy-End Petroleum Distillates", Laramie Energy Research Center, Analytical Chemistry, 44(8), p. 1391 (Jul. 1972).

Karlsen, D. A. et al., "Analysis of petroleum fractions by TLC-FID: applications to pertroleum reservoir description", Org. Geochem 17(5), pp. 603-617 (1991).

Schabron, J. F. et al, Total Pericondensed Aromatic (TPA) Determination as an Alternative to Gravimetric Asphaltenes, Prepr. Pap.-Am. Chem. Soc. Div. Pet. Chem., 56(1), 38 (2001).

Rogel, E. et al., "Determination of Asphaltenes in Crude Oil and Petroleum Products by the on Column Precipitation Method", Energy Fuels, 23, pp. 4515-4521 (2009).

"Energy and Environmental Profile of the US Petroleum Refining Industry", Prepared by Energetics Inc. for U.S. Department of Energy Office of Industrial Technologies, pp. 4-5, 27, 33, 49 and 62-63.

"Standard Test Method for Molecular Weight (Relative Molecular Mass) of Hydrocarbons by Thermoelectric Measurement of Vapor Pressure," ASTM Designation: D 2503-82 (Reapproved 1997), pp. 871-873.

Anderson, S.I. et al., "Aggregation of Asphaltenes as Determined by Calorimetry", Journal of Colloid and Interface Science, 142, pp. 497-502 (1991).

Barton, A.F., "Solubility Parameters", Chemical Reviews, 75(6), pp. 731-753 (1974).

Magaril, R. Z. et al., Study of the Mechanism of Coke Formation in the Cracking of Petroleum Resins, International Chemical Engineering 8(4), p. 727.

Schabron, J.F. et al. Predicting Coke Formation Tendencies, Fuel 80 (2001) 1435-1446.†

\* cited by examiner
† cited by third party

METHOD FOR PREDICTING CATALYST PERFORMANCE

BACKGROUND OF THE INVENTION

1. Technical Field

The present invention generally relates to a method for predicting catalyst performance in catalyst processes in the refining and petrochemical industry.

2. Description of the Related Art

Hydroprocessing, which includes by way of example hydroconversion, hydrocracking, hydrotreating, hydrogenation, hydrofinishing and hydroisomerization, plays an important role in upgrading petroleum feedstocks to meet the more stringent quality requirements. For example, there is an increasing demand for improved hetero-atom removal, aromatic saturation, and boiling point reduction as well as removal of metal contaminants such as vanadium and nickel. Much work is presently being done in hydrotreating because of greater demands for the removal of undesirable components such as heteroatoms, most notably sulfur, from transportation and heating fuel streams. Hydrotreating is well known in the art and usually involves treating the petroleum streams with hydrogen in the presence of a supported catalyst at hydrotreating conditions.

Hydrocarbon feedstocks likewise generally contain polar core materials, i.e., polyaromatics such as asphaltenes, dispersed in lower polarity solvent(s). Intermediate polarity material(s), usually referred to as resin(s), can associate with the polar core materials to maintain a homogeneous mixture of the components.

Asphaltenes are organic heterocyclic macromolecules which occur in crude oils. Under normal reservoir conditions, asphaltenes are usually stabilized in the crude oil by maltenes and resins that are chemically compatible with asphaltenes, but that have lower molecular weight. Polar regions of the maltenes and resins surround the asphaltene while non-polar regions are attracted to the oil phase. However, changes in pressure, temperature or concentration of the crude oil can alter the stability of the dispersion and increase the tendency of the asphaltenes to agglomerate into larger particles. As these asphaltene agglomerates grow, so does their tendency to precipitate out of solution.

One of the problems encountered in crude oil production and refining is coking. Processes that utilize catalysts to process a hydrocarbon-containing material containing one or more polyaromatic compound suffer significantly from catalyst aging due to coke deposition on the catalyst over time. In general, as the one or more polyaromatic compound precipitate out of the hydrocarbon-containing feed during hydroprocessing, the precipitated polyaromatic(s) deposit onto the catalyst and form coke. As the coke that is formed on the catalyst progresses over time, plugging of the catalyst pores and covering of the surface of the catalyst occurs. In time, the coked catalyst loses its catalytic activity and, ultimately, must be replaced.

Accordingly, it would be advantageous to predict catalyst performance in the refining and petrochemical industry in a method that can be carried out in a simple, cost efficient and repeatable manner.

SUMMARY OF THE INVENTION

In accordance with one embodiment of the present invention, there is provided a method comprising the steps of:
(a) precipitating an amount of polyaromatic compounds from a liquid sample of a first hydrocarbon-containing feedstock having solvated polyaromatic compounds therein with one or more first solvents in a column;
(b) determining one or more solubility characteristics of the precipitated polyaromatic compounds;
(c) analyzing the one or more solubility characteristics of the precipitated polyaromatic compounds; and
(d) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the first hydrocarbon-containing feedstock.

In accordance with a second embodiment of the present invention, there is provided a method comprising the steps of:
(a) precipitating an amount of polyaromatic compounds from a liquid sample of a first hydrocarbon-containing feedstock having solvated polyaromatic compounds therein with one or more first solvents in a column;
(b) determining one or more solubility characteristics of the precipitated polyaromatic compounds;
(c) analyzing the one or more solubility characteristics of the precipitated polyaromatic compounds; and
(d) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the first hydrocarbon-containing feedstock; and
(e) selecting a second hydrocarbon-containing feedstock sample; repeating steps (a)-(d); and comparing the results of the second hydrocarbon-containing feedstock sample with the results of the first hydrocarbon-containing feedstock sample to predict a leading candidate hydrocarbon-containing feedstock.

In accordance with a third embodiment of the present invention, there is provided a method comprising the steps of:
(a) selecting one or more hydrocarbon-containing feedstocks, wherein the selection of the one or more hydrocarbon-containing feedstocks comprises:
 (i) precipitating an amount of polyaromatic compounds from a liquid sample of a first hydrocarbon-containing feedstock having solvated polyaromatic compounds therein with one or more first solvents in a column;
 (ii) determining one or more solubility characteristics of the precipitated polyaromatic compounds;
 (iii) analyzing the one or more solubility characteristics of the precipitated polyaromatic compounds; and
 (iv) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the first hydrocarbon-containing feedstock; and
(b) feeding the selected one or more hydrocarbon-containing feedstocks to one or more crude hydrocarbon refinery components.

In accordance with a fourth embodiment of the present invention, there is provided a system comprising: (a) one or more crude hydrocarbon components; and (b) one or more hydrocarbon-containing feedstocks in fluid communication with the one or more crude hydrocarbon refinery components, wherein the one or more hydrocarbon-containing feedstocks are selected by a process comprising:

(i) precipitating an amount of polyaromatic compounds from a liquid sample of a first hydrocarbon-containing feedstock having solvated polyaromatic compounds therein with one or more first solvents in a column;

(ii) determining one or more solubility characteristics of the precipitated polyaromatic compounds;

(iii) analyzing the one or more solubility characteristics of the precipitated polyaromatic compounds; and (iv) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the first hydrocarbon-containing feedstock.

The methods of the present invention advantageously predict catalyst performance of a catalyst in a refinery operation such as hydroprocessing of a hydrocarbon-containing feedstock in a simple, cost efficient and repeatable manner. Accordingly, a leading candidate hydrocarbon-containing feedstock can be readily determined based on the predicted performance of a catalyst in a refinery operation in order to, for example, minimize fouling or coking during the refinery operation, adjust the operating conditions to maximize conversion to desired products and extend catalyst life.

DETAILED DESCRIPTION OF THE PREFERRED EMBODIMENTS

In one embodiment, a method of the present invention involves (a) precipitating an amount of polyaromatic compounds from a liquid sample of a first hydrocarbon-containing feedstock having solvated polyaromatic compounds therein with one or more first solvents in a column; (b) determining one or more solubility characteristics of the precipitated polyaromatic compounds; (c) analyzing the one or more solubility characteristics of the precipitated polyaromatic compounds; and (d) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the hydrocarbon-containing feedstock. The term "catalyst performance" as used herein shall be understood to mean the susceptibility to fouling or coking of the catalyst during a refinery operation. Coking (by way of polyaromatic compound precipitation) is one of several mechanisms that can cause catalyst activity performance to decline more rapidly than expected. Coke deposition on the catalyst surface occurs naturally and, in the majority of the design configurations, this process is irreversible.

Generally, the source of the hydrocarbon-containing feedstock having solvated polyaromatic compounds therein may be any source where such a hydrocarbon-containing feedstock may be obtained, produced, or the like. The feedstock can be any feedstock falling into the hydrocarbon boiling range such as, for example, naphtha, jet, kerosene, diesel, VGO, lubes and atmospheric and vacuum residues. The source may be one or more producing wells in fluid communication with a subterranean oil reservoir. The producing well(s) may be under thermal recovery conditions, or the producing well(s) may be in a heavy oil field where the hydrocarbon crude or oil is being produced from a reservoir having a strong water-drive.

In one embodiment, the hydrocarbon-containing feedstock sample includes any heavy hydrocarbons such as heavy crude oil, heavy hydrocarbons extracted from tar sands, commonly called tar sand bitumen, such as Athabasca tar sand bitumen obtained from Canada, heavy petroleum crude oils such as Venezuelan Orinoco heavy oil belt crudes, Boscan heavy oil, Hamaca crude oil, heavy hydrocarbon fractions obtained from crude petroleum oils, particularly heavy vacuum gas oils, vacuum residuum as well as petroleum tar, tar sands and coal tar. Other examples of heavy hydrocarbon feedstocks which can be used are oil shale, shale, coal liquefaction products and the like.

In another embodiment, the hydrocarbon-containing feedstock sample includes any solid hydrocarbon-containing deposit such as asphaltene solids from, e.g., refinery production preparation or an oil facility.

In another embodiment, the hydrocarbon-containing feedstock sample includes any processed sample such as heavy cycle gas oil (HCGO), LC Fining ebullated bed hydrocracked products, fluid catalytic cracking (FCC) products and the like.

In another embodiment, the hydrocarbon-containing feedstock sample includes any middle distillate feedstock. A middle distillate refers in particular to those mineral oils which are obtained by distilling crude oil and boil within the range from 120 to 450° C. such as, for example, kerosene, jet fuel, diesel, naphtha, heating oil and the like. A middle distillate can also include vacuum gas oil with a boiling range between 450° C. and 550° C. and vacuum residue with a boiling range higher than 550° C.

In one embodiment, the polyaromatic compounds in the hydrocarbon-containing feedstock sample include asphaltenes. Asphaltenes, sometime also referred to as asphaltenes, are a mixed solubility class of compounds as opposed to a chemical class of compounds, generally solid in nature and comprise polynuclear aromatics present in the solution of smaller aromatics and resin molecules, and are also present in the crude oils and heavy fractions in varying quantities. Asphaltenes do not usually exist in all of the condensates or in light crude oils; however, they are present in relatively large quantities in heavy crude oils and petroleum fractions. Asphaltenes are insoluble components or fractions and their concentrations are defined as the amount of asphaltenes precipitated by addition of an n-paraffin solvent to the feedstock which are completely soluble in aromatic solvents such as Toluene, benzene, xylenes and the likes, as prescribed in the Institute of Petroleum Method IP-143.

In one embodiment, the polyaromatic compounds in the hydrocarbon-containing feedstock sample include 2,3-benzanthracene, pentacene, hexacene, acenaphthene, acenaphthylene, anthracene, benz[a]anthracene, benzo[a]pyrene, benzo[ghi]perylene, benzo[j]fluoranthene, benzo[k]fluoranthene, chrysene, Coronene, dibenz(a,h)anthracene, benzo[e]

pyrene, benzo[b]fluoranthene, fluoranthene, indeno(1,2,3-cd)pyrene, phenanthrene, pyrene and the like and mixtures thereof.

In general, a liquid sample of a first hydrocarbon-containing feedstock having solvated polyaromatic compounds therein is first provided. As one skilled in the art will readily understand, it may be necessary to add a solvent to the hydrocarbon-containing feedstock in order for the sample to be sufficiently fluid enough to be passed through the column. Useful solvents include any solvent in which the hydrocarbon-containing feedstock sample is soluble or which is capable of allowing the hydrocarbon-containing feedstock sample to be sufficiently fluid to be passed through the column. Representative examples of such solvents include one or more chlorinated hydrocarbon solvents, one or more aromatic hydrocarbon solvents, one or more ether solvents, one or more alcohol solvents and the like and mixtures thereof. Suitable chlorinated hydrocarbon solvents include, but are not limited to, dichloromethane, 1,2-dichloroethane, chloroform, carbon tetrachloride and the like and mixtures thereof. Suitable aromatic hydrocarbon solvents include, but are not limited to, benzene, toluene, xylene and the like and mixtures thereof. Suitable ether solvents include tetrahydrofuran, diethylether, dioxane and the like and mixtures of thereof. Suitable alcohol solvents include low molecular weight aliphatic alcohols such as methanol, ethanol, isopropanol and the like and mixtures thereof.

In one embodiment, the sample solution can be prepared from about 10 to about 50 wt. % solution of the hydrocarbon-containing feedstock sample in the solvent(s).

Initially, at least a portion of the sample solution is injected into a column. Generally, the column will have an inlet and an outlet and can be any type of column which is hollow and permits the flow of an aqueous-type material through the interior of the column. The column can be any size and cross sectional shape, e.g., the column can be cylindrical, square, rectangular, triangular, or any other geometrical shape as long as it is hollow and permits the passing of aqueous-type material. In one embodiment, the column is cylindrical. Furthermore, the column can be of any suitable length and any inner diameter or inner cross-sectional area. In one embodiment, the column can have a diameter of from about 0.25 inches (0.63 cm) to about 1 inch (2.5 cm) and a length of from about 50 mm to about 500 mm. One skilled the art could envisage that the column can generally be any inert filtration device for use in the methods of the present invention.

Any suitable material may be selected for use as the column. For example, the column can be formed of a relatively inert or chemically unreactive material such as glass, stainless steel, polyethylene, polytetrafluoroethylene (PTFE), polyaryletheretherketone, (PEEK), silicon carbide or mixtures of thereof, for example, a PEEK-lined stainless steel column.

The column may be vertical or horizontal or arranged in any suitable way, provided that it can be loaded with the sample solution and that the appropriate solvent(s) can be passed through it. As will be understood by those of ordinary skill in the art, a pump may also be used to increase the flow rate through the column.

In another embodiment, an inert packing material is included within the column. The amount of the inert packing material should not exceed an amount which will prevent the passing of any liquid containing material through the column. The packed column advantageously allows for the use of a relatively small volume of sample solution and solvent(s). Suitable inert packing material includes any material that is inert to asphaltene irreversible adsorption. Examples of such materials include fluorinated polymers such as, for example, polyvinylidene fluoride (PVDF), fluorinated ethylene propylene (FEP), polytetrafluoroethylene (PTFE), silicon carbide, polydivinylbenzene (PDVB) and the like and mixtures thereof.

Once the sample solution has been passed into the column, one or more first solvents are then passed through the column. Useful one or more first solvents are typically alkane mobile phase solvent(s) and can be determined by one skilled in the art. In one embodiment, the alkane mobile phase solvent is n-heptane. However, other alkane mobile phase solvents such as, for example, iso-octane, n-pentane or n-hexane may be used.

The one or more first solvents should be passed into the column for a time period sufficient to elute the alkane soluble fraction, e.g., maltenes or petrolenes in the case where the polyaromatic compounds are asphaltenes, and induce precipitation of the alkane insoluble fraction such as precipitated asphaltenes, from the hydrocarbon-containing feedstock sample. The alkane soluble fraction are typically the least polar of the polyaromatic compounds. Generally, once the alkane mobile phase solvent (i.e., one or more first solvents) enters the column, the alkane mobile phase solvent dilutes and displaces the solvent in the sample solution, thereby allowing the polyaromatic compounds having a polarity greater than the alkane soluble fraction, e.g., asphaltenes, to substantially precipitate therefrom. The alkane soluble fraction then elutes from the column.

In accordance with the present invention, one or more solubility characteristics of the precipitated polyaromatic compounds are determined once substantially all of the alkane soluble fraction has eluted. The one or more solubility characteristics of the precipitated polyaromatic compounds to be determined include, by way of example, solubility parameters, miscibility numbers, kauri-butanol numbers, dipole moments, relative permitivities, polarity indexes, refractive indexes and specific types of intermolecular interaction in liquid media such as acid and base numbers. Various ways to determine the one or more solubility characteristics of the precipitated polyaromatic compounds are within the purview of one skilled in the art. For example, solubility characteristics of the precipitated polyaromatic compounds can be determined according to the following methods: Solubility Fraction Method; and Solubility Profile Method.

Solubility Fraction Method

The solubility fraction method involves the step of determining one or more solubility characteristics of the precipitated polyaromatic compounds by (1) dissolving at least part of the amount of the precipitated polyaromatic compounds in one or more second solvents having a solubility parameter at least 0.7 $MPa^{0.5}$ higher than the one or more first solvents; and (2) dissolving a second amount of the precipitated polyaromatic compounds in one or more third solvents having a solubility parameter higher than the one or more second solvents, wherein the solubility parameter of the one or more third solvents is at least about 21 $MPa^{0.5}$ but no greater than about 30 $MPa^{0.5}$. A solubility parameter as described herein is determined by the Hansen's methodology described in Barton, A. F. M. *Handbook of Solubility Parameters and Other Cohesion Parameters*; CRC Press Inc.: Boca Raton, Fla., p. 95 (1983).

Suitable one or more second solvents having a solubility parameter at least 0.7 $MPa^{0.5}$ higher than the one or more first solvents can be determined by one skilled in the art. Useful solvents include, but are not limited to, one or more alkane solvents, one or more chlorinated hydrocarbon solvents, one or more aromatic solvents, one or more ether solvents, one or more alcohol solvents and the like and mixtures thereof.

Representative examples of such solvents can be any of those disclosed above. It is also contemplated that blends of such solvents can be used. In one embodiment, a blend can contain from about 0.5 wt. % to about 99.5 wt. % chlorinated solvent and from about 99.5 wt. % to about 0.5 wt. % alkane solvent. In another embodiment, a blend can contain from about 10 wt. % to about 25 wt. % chlorinated solvent and from about 90 wt. % to about 75 wt. % alkane solvent.

Suitable one or more third solvents having a solubility parameter higher than the one or more second solvents, wherein the solubility parameter of the one or more third solvents is at least about 21 MPa$^{0.5}$ but no greater than about 30 MPa$^{0.5}$, can be determined by one skilled in the art. Generally, the one or more third solvents will dissolve any remaining precipitated polyaromatic compounds in the column. Useful solvents include, but are not limited to, one or more alcohol solvents, one or more chlorinated hydrocarbon solvents, one or more aromatic solvents, one or more ether second solvents and the like and mixtures thereof. Representative examples of such solvents can be any of those disclosed above. It is also contemplated that blends of such solvents can be used. In one embodiment, a blend can contain from about 0.5 wt. % to about 99.5 wt. % chlorinated solvent and from about 99.5 wt. % to about 0.5 wt. % alcohol solvent. In another embodiment, a blend can contain from about 80 wt. % to about 95 wt. % chlorinated solvent and from about 20 wt. % to about 5 wt. % alcohol solvent.

If desired, one or more additional solvents or solvent blends can be added to dissolve at least part of the amount of the precipitated polyaromatic compounds after the addition of the one or more second solvents and before the addition of the one or more third solvents. In general, the one or more additional solvents or solvent blends will have a solubility parameter greater than the previously added one or more solvents or solvent blends and less than the solubility parameter of the one or more third solvents. For example, one or more fourth solvents having a solubility parameter between the solubility parameter of the one or more second solvents and the solubility parameter of the one or more third solvents can be added to dissolve at least part of the amount of the precipitated asphaltenes. In another embodiment, one or more fifth solvents having a solubility parameter between the solubility parameter of the one or more fourth solvents and the solubility parameter of the one or more third solvents can be added to dissolve at least part of the amount of the precipitated asphaltenes. In yet another embodiment, one or more sixth solvents having a solubility parameter between the solubility parameter of the one or more fifth solvents and the solubility parameter of the one or more third solvents can be added to the dissolve at least part of the amount of the precipitated asphaltenes.

Suitable additional solvents include, but are not limited to, one or more alkane solvents, one or more chlorinated hydrocarbon solvents, one or more alcohol solvents, one or more aromatic solvents and the like and mixtures thereof. Representative examples of such solvents can be any of those disclosed above.

The polyaromatic compound concentration in the eluted fractions from the column is continuously monitored using, for example, a liquid chromatography detector which generates a signal proportional to the amount of each eluted fraction and is recorded in a manner well known in the art. There are a number of commercially available liquid chromatography detectors that can be used including, e.g., refractive index detectors, mass spectrometry, liquid chromatography/mass spectrometry, NMR spectroscopy, Raman spectroscopy, infrared spectroscopy, fluorescence spectroscopy, UV-Vis spectroscopy, diode array detector, Charged Aerosol, evaporative light scattering detectors (ELSD) and the like; all of which can be used in the methods described herein. Other online detectors are known to those skilled in the art. Quantification can then be performed using methods known in the art, e.g., using commercially-available computer programs.

In one preferred embodiment, an evaporative light scattering detector is used as a liquid chromatography detector to monitor each eluting sample's concentration to determine the solubility characteristics of the precipitated polyaromatic compounds. The operating principle of an evaporative light scattering detector is as follows: the compounds to be analyzed are transported by a mobile phase or a more volatile carrier liquid which is then nebulized and evaporated at a relatively low temperature (being able to be in the order of from about 30 to about 150° C.) so that residual microparticles alone remain—ideally the compounds to be analyzed—which can be detected by light scattering. In this manner, it is possible to analyze directly effluents which originate from the column under the condition of selecting a mobile phase which is volatile enough to be directly used as a carrier liquid for the evaporative light scattering detector. For example, in the case of the asphaltenes for the solubility fraction method, the result is a single peak for each eluted solvent fraction with each peak representing a solubility characteristic of the asphaltenes.

Solubility Profile Method

The solubility profile method involves the step of determining one or more solubility characteristics of the precipitated polyaromatic compounds. For example, in the case of where the polyaromatic compounds are asphaltenes, the method involves dissolving a first amount and a second amount of the precipitated asphaltenes by gradually and continuously changing the alkane mobile phase solvent to a final mobile phase solvent having a solubility parameter at least 1 MPa$^{0.5}$ higher than the alkane mobile phase solvent. Generally, the first amount of the precipitated asphaltenes (also referred to as "easy to dissolve asphaltenes") will have a lower solubility parameter than the second amount of asphaltenes (also referred to as "hard to dissolve asphaltenes"). The term "gradually" as used herein shall be understood to mean that the alkane mobile phase solvent is incrementally removed from the column over a period of time by continuously adding a final mobile phase solvent having a solubility parameter at least 1 MPa$^{0.5}$ higher than the alkane mobile phase solvent to the column. Generally, gradually and continuously changing from essentially the alkane mobile phase solvent to the final mobile phase solvent can occur during a period of about 5 minutes to about 120 minutes at a flow rate of about 1 mL/min. to about 4 mL/min. In one embodiment, gradually and continuously changing from the alkane mobile phase solvent to the final mobile phase solvent can occur during a period of about 15 minutes to about 30 minutes at a flow rate of about 1 mL/min. to about 4 mL/min.

The first amount of the precipitated asphaltenes are dissolved by gradually and continuously changing the alkane mobile phase solvent to a first final mobile phase solvent having a solubility parameter at least 1 MPa$^{0.5}$ higher than the alkane mobile phase solvent. As one skilled in the art will readily appreciate, the selection of the first final mobile phase solvent will depend on such factors as moving from a low solubility parameter solvent (low solvent power) to a high solubility parameter solvent (high solvent power) using solvents that have the right combination of dispersion, polar and hydrogen bonding forces. For example, a first final mobile phase solvent such as a chlorinated hydrocarbon solvent, e.g., dichloromethane, an ether solvent, an aromatic hydrocarbon solvent or mixtures thereof is gradually and continuously added to the column to sequentially change the alkane mobile phase solvent from 100% alkane mobile phase solvent to 100% first final mobile phase solvent, i.e., the alkane mobile phase solvent is changed to 1% dichloromethane in 99% alkane mobile phase solvent, then to 2% dichloromethane in 98% alkane mobile phase solvent, until the mobile phase solvent in the column is 100% dichloromethane and 0% alkane mobile phase solvent. In this manner, a first amount of the precipitated asphaltenes (i.e., easy to dissolve asphaltenes) will be gradually dissolved and a characteristic elution pattern generated, which is referred to as the asphaltene solubility profile, as discussed hereinbelow.

After the first amount of precipitated asphaltenes has been gradually dissolved, a second or remaining amount of the precipitated asphaltenes (which are not capable of being redissolved in the one or more first final mobile phase solvents) is left in the column. Thus, in order to redissolve the second amount of precipitated asphaltenes, also referred to as hard to dissolve asphaltenes (i.e., higher solubility parameter asphaltenes), it is may be necessary to add one or more second final mobile phase solvents having a solubility parameter at least 1 MPa$^{0.5}$ higher than the first final mobile phase solvent to the column in order to substantially dissolve the remaining amount of the precipitated asphaltenes in the column and generate a characteristic elution pattern of the hydrocarbon-containing material. This can advantageously allow for a more accurate determination of the solubility profile of the various asphaltene components in the hydrocarbon-containing material.

The selection of the second final mobile phase solvent will depend on such factors as moving from a lower solubility parameter solvent (the first final mobile phase solvent) to a higher solubility parameter solvent (the second final mobile phase solvent) using solvents that have the right combination of dispersion, polar and hydrogen bonding forces. A suitable one or more second final mobile phase solvent can readily be determined by one skilled in the art, e.g., a $C_1$ to $C_6$ alcohol such as methanol. Accordingly, in one embodiment, methanol is gradually and continuously added to the column to sequentially change the first final mobile phase solvent, e.g., dichloromethane, from 100% dichloromethane to 100% methanol, i.e., dichloromethane is first changed to 1% methanol in 99% dichloromethane, then to 2% methanol in 98% dichloromethane, until the second final mobile phase solvent in the column is 100% methanol and 0% dichloromethane.

The flow rate and time period for gradually and continuously adding the one or more second final mobile phase solvents are substantially the same as for the first final mobile phase solvents.

The asphaltene concentration in the eluted fractions from the column is continuously monitored using, for example, a liquid chromatography detector as discussed hereinabove. In one preferred embodiment, an evaporative light scattering detector is used as a liquid chromatography detector to monitor each eluting sample's concentration. The operating principle of an evaporative light scattering detector is as follows: the compounds to be analyzed are transported by a mobile phase or a more volatile carrier liquid which is then nebulized and evaporated at a relatively low temperature (being able to be in the order of from about 30 to about 150° C.) so that residual micro-particles alone remain—ideally the compounds to be analyzed—which can be detected by light scattering. In this manner, it is possible to analyze directly effluents which originate from the column under the condition of selecting a mobile phase which is volatile enough to be directly used as a carrier liquid for the evaporative light scattering detector. For example, in the case of the asphaltenes, the result is a curve that represents the solubility parameter distribution of the asphaltenes.

Next, a solubility profile of the asphaltenes in the liquid sample can be created by techniques known in the art. For example, when asphaltenes are quantified using an evaporative light scattering detector, the result is a curve that represents the solubility parameter distribution of the asphaltene in the hydrocarbon-containing material. Since the solubility parameter of a mixture of solvents is given by the volumetric average of the components, it is possible to convert the time scale of the elution to a solubility parameter scale using the following equation:

$$\delta = \sum_{i=1}^{n} \phi_i \delta_i$$

wherein $\delta$ is the solubility profile of the mixture, $\phi_i$ is the volume fraction and $\delta_i$ is the solubility parameter of each of the components, respectively. The volume fraction is the volume fraction of the blend of each solvent and readily determined by the chromatography apparatus. The solubility parameter of a component is either known in the art, e.g., Barton, A. F. M. *Handbook of Solubility Parameters and Other Cohesion Parameters*; CRC Press Inc.: Boca Raton, Fla., 1983, or can be determined by techniques within the purview of one skilled in the art.

Determining Polyaromatic Content

Once the one or more solubility characteristics have been analyzed for a given hydrocarbon-containing feedstock sample, the polyaromatic compound content can be determined as follows.

Solubility Fraction Method

In the solubility fraction method, the result is one peak for each eluted solvent fraction with each peak representing a solubility characteristic of the polyaromatic compound. The area under the separate peaks can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Then, each area is correlated to a polyaromatic compound mass according to a calibration curve that depends on the type of detector used as within the purview of one skilled in the art. The calibration may or may not be the same for all the peaks. Thus, the total polyaromatic compound mass can be determined for each peak. Then, if necessary, the total polyaromatic compound mass (TAM) for the sample would be the addition of all the polyaromatic compound masses (A) determined for each peak:

$$TAM = \sum_{i=1}^{n} A_i$$

Solubility Profile Method

In the solubility profile method, the amount of polyaromatic compound is determined by calculating the area of the second peak of the solubility profile. For example, an asphaltene solubility profile normally shows either two peaks or one peak and one shoulder from the evaporative light scattering detector. The two peaks or peak/shoulder can be separated by numerical methods well known in the art such as, for example, peak deconvolution or peak fitting. The area under the peaks, e.g., the second peak, can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Then, this area is correlated to an asphaltene mass according to a calibration curve. A calibration procedure was developed that relates the measured peak area (Area) to the total asphaltene mass in the sample (TAM). The following equation is an example of such correlation that allows the calculation of the asphaltene mass:

$$\text{Log TAM} = 0.5336 \log A - 6.097$$

where TAM is the total mass in the sample and A is the area of the second deconvoluted peak respectively.

Predicting Catalyst Performance

Once one or more solubility characteristics have been analyzed for a given hydrocarbon-containing feedstock sample, a mathematical parameter derived from the one or more solubility characteristics is correlated with one or more measurements of catalyst activity performance of the hydrocarbon-containing feedstock to predict catalyst performance of a catalyst in a refinery operation of the hydrocarbon-containing feedstock. A refinery operation is well known to one skilled in the art and can involve, for example, feeding one or more hydrocarbon-containing feedstocks in one or more crude hydrocarbon refining components within a refinery. For example, the hydrocarbon-containing feedstocks can be subjected to one or more conventional hydroprocessing techniques such as hydrotreating, hydrocracking, hydrogenation, hydrofinishing and hydroisomerization and the like. The refinery hydroprocesses that the one or more of the hydrocarbon-containing feedstocks can be used in are well known in the art.

The term "crude hydrocarbon refinery component" generally refers to an apparatus or instrumentality of a process to refine crude hydrocarbons, such as an oil refinery process. Crude hydrocarbon refinery components include, but are not limited to, heat transfer components such as a heat exchanger, a furnace, a crude preheater, a coker preheater, or any other heaters, a FCC slurry bottom, a debutanizer exchanger/tower, other feed/effluent exchangers and furnace air preheaters in refinery facilities, flare compressor components in refinery facilities and steam cracker/reformer tubes in petrochemical facilities. Crude hydrocarbon refinery components can also include other instrumentalities in which heat transfer may take place, such as a fractionation or distillation column, a scrubber, a reactor, a liquid-jacketed tank, a pipestill, a coker and a visbreaker. It is understood that "crude hydrocarbon refinery components," as used herein, encompass tubes, piping, baffles and other process transport mechanisms that are internal to, at least partially constitute, and/or are in direct fluid communication with, any one of the above-mentioned crude hydrocarbon refinery components.

A mathematical parameter derived from the one or more solubility characteristics can include calculating a percentage of the peak area for the amount of dissolved polyaromatic compounds having the highest polarity relative to the total peak areas, wherein the peak areas are derived from the signals generated from the detector. Other mathematical parameters derived from the one or more solubility characteristics are within the purview of one skilled in the art and illustrated in the examples herein. Various ways to correlate the one or more measurements of catalyst activity performance of the hydrocarbon-containing feedstock with the one or more mathematical parameters are also within the purview of one skilled in the art and illustrated in the examples. However, other ways to correlate the one or more measurements of catalyst activity performance of the hydrocarbon-containing feedstock with the one or more mathematical parameters can readily be determined by one skilled in the art.

The one or more measurements of catalyst activity performance for the hydrocarbon-containing feedstock samples can be any known measurement of catalyst activity performance, such as those disclosed in, for example, Murray, M. R. "Upgrading Petroleum Residues and Heavy Oil", Dekker, New York, (1994) and Gray, M. R., Energy & Fuels, 17, p. 1566 (2003). As one skilled in the art will readily understand, the type of catalyst being evaluated for catalyst performance will necessary depend on the measurement of catalyst activity performance. For example, the performance of a catalyst used in a hydrotreating/hydrodenitrogenation catalyst system can be determined according to the methods described herein using a measurement in terms of hydrodenitrogenation (HDN) rate. The catalysts used in a refinery operation of a hydrocarbon-containing feedstock are well known in the art and any such catalysts can be evaluated for performance based on the measurement of catalyst activity performance. Activity performance is one indicator (requiring short-term measurement) among other things one of which is the lower degree of susceptibility to fouling or coking (from a longer term measurement).

Accordingly, a measurement of catalyst activity performance includes, by way of example, one or more measurements in terms of hydrodenitrogenation (HDN) rate, hydrodesulfurization (HDS) rate, hydrodeoxygenation (HDO) rate, hydrogenation rate, hydrodemetallation (HDM) rate, % carbon residue reduction (CRR), % microcarbon residue reduction (MCR), % residue conversion, increase in H/C ratio, reduction of molecular weights, changes in the percentages of Saturates, Aromatics, Resins, and Asphaltenes (SARA) fractions, increase in API such as increase in API gravity, reduction in density and the like.

In one embodiment, a measurement can be in terms of hydrodenitrogenation (HDN) rate ($h^{-1}$), hydrodesulfurization (HDS) rate ($h^{-1}$), hydrodeoxygenation (HDO) ($h^{-1}$), hydrogenation rate ($h^{-1}$), hydrodemetallation (HDM) rate ($h^{-1}$) including the removal of nickel compounds (HDNi) and vanadium compounds (HDV), % carbon residue reduction (CRR), % microcarbon residue reduction (MCR), % residue conversion such as atmospheric (AR) or vacuum residue (VR) conversion, H/C ratio, molecular weight, changes in SARA (Saturates, Aromatics, Resins, and Asphaltenes) fractions, increase in API or reduction in density (gr/L), aromatic content, hydrogen content, and the like. The one or more measurements of catalyst activity performance for the hydrocarbon-containing feedstock samples can readily be determined by methods known to one skilled in the art and are exemplified in the examples.

In one embodiment, after correlating the one or more measurements of catalyst activity performance for the hydrocarbon-containing feedstock with the one or more of the parameters related to asphaltene stability, a different sample of the same hydrocarbon-containing feedstock can be characterized for catalyst performance and then these results can be compared against the original hydrocarbon-containing feedstock for the purpose of, for example, quality control. A different sample can be from the same batch of the hydrocarbon-containing feedstock or can be from a different reservoir, field, country or continent. The various ways to compare the two hydrocarbon-containing feedstocks include comparing their API gravity, sulfur content, vanadium and nickel contents, distillable material contents, viscosity, asphaltene content, "easy-to-react" to "hard-to-process" asphaltenes, H/C ratio, molecular weight, SARA (Saturates, Aromatics, Resins, and Asphaltenes), Total Acid Number etc.

In another embodiment, the method of the present invention further includes the step of generating a cost value for the first hydrocarbon-containing feedstock sample or one or more of the leading candidates. The cost value can be generated based on factors such as API gravity, sulfur content, vanadium and nickel contents, distillable material contents, viscosity, asphaltene content, Total Acid Number, aromatic content, hydrogen content, etc. The cost value generated for the first hydrocarbon-containing feedstock sample can then be compared with a market price of the same or different hydrocarbon-containing feedstock. In this manner, one can determine if the one or more hydrocarbon-containing feedstocks tested in the methods described herein are comparable to their market price.

The information obtained from the methods of the present invention can then be stored in a relational database. For example, a relational database can be electrically connected to a signal data collector comprising a computer microprocessor for system operation and control to collect the data from the various tests over an extended period of time to compile a library therefrom. The database can be used to find optimum combinations for a desired product stream, and can be particularly useful when the desired product stream varies depending on market factors. When the product requirements change, appropriate combinations can be selected to prepare the desired product.

Once one or more of the hydrocarbon-containing feedstocks have been selected, one or more of the selected hydrocarbon-containing feedstocks can then be used as a refinery feedstock in one or more crude hydrocarbon refining components within a refinery and subjected to one or more conventional hydroprocessing techniques such as hydrotreating, hydrocracking, hydrogenation, hydrofinishing and hydroisomerization and the like. Alternatively, one or more of the selected hydrocarbon-containing feedstocks can be blended with one or more of the same or different hydrocarbon-containing feedstocks. The refinery hydroprocesses that the one or more of the selected hydrocarbon-containing feedstocks can be used in are well known in the art. A crude hydrocarbon refinery component include those discussed above.

In one embodiment, representative examples of such crude hydrocarbon refinery components include a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank, a visbreaker and the like.

Accordingly, another embodiment of the present invention is directed to a method involving:

(a) selecting one or more hydrocarbon-containing feedstocks, wherein the selection of the one or more hydrocarbon-containing feedstocks comprises:

(i) precipitating an amount of polyaromatic compounds from a liquid sample of a first hydrocarbon-containing feedstock having solvated polyaromatic compounds therein with one or more first solvents in a column;

(ii) determining one or more solubility characteristics of the precipitated polyaromatic compounds;

(iii) analyzing the one or more solubility characteristics of the precipitated polyaromatic compounds; and (iv) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the hydrocarbon-containing feedstock; and (b) feeding the selected one or more hydrocarbon-containing feedstocks to one or more crude hydrocarbon refinery components.

If desired, the selection of the one or more hydrocarbon-containing feedstocks can further employ one or more additional steps as discussed above, such as step (v) selecting one or more second hydrocarbon-containing feedstock samples; repeating steps (i)-(iv); and comparing the results of the one or more second hydrocarbon-containing feedstock samples with the results of the first hydrocarbon-containing feedstock sample to determine one or more leading candidate hydrocarbon-containing feedstocks.

The following non-limiting examples are illustrative of the present invention.

Example 1

Solutions of three reference feedstocks shown in Table 1 were prepared by dissolving 5.00 g of the feedstocks in 10 mL of methylene chloride. The solutions were injected into a separate stainless steel column packed with poly(tetrafluoroethylene) (PTFE) using a heptane mobile phase (Solubility Parameter of 15.3 MPa0.5) at a flow rate of 4 mL/min. The maltenes (heptane solubles) eluted from the column as the first peak around 2 minutes after the injection. The mobile phase was then switched to a blend of 10% methanol/90% dichloromethane (Solubility Parameter of 21.23 MPa0.5). In this manner, the asphaltene contents were measured with a total analysis time of approximately 20 to 22 minutes.

The eluted fractions were quantified using an Evaporative Light Scanning Detector (ELSD) operating at the following conditions: drift tube temperature 75° C.; volumetric flow of the solvents was 4.0 mL/min. and 3.5 L/min. of nitrogen as the nebulizing gas. The light scattered by the non-volatile particles was collected and is a measure of the concentration of the solute in the column effluent. For the case of asphaltenes, the measurement of the light scattered, also known as response, can be correlated with the asphaltenes content in the sample.

Figure 1:
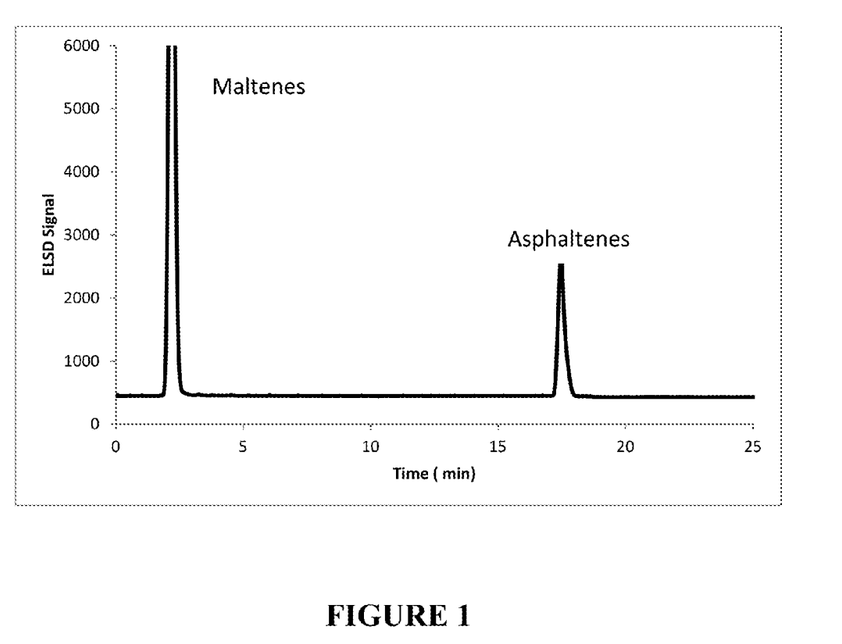
FIG. 1 is a graph showing the total asphaltenes for the references feedstocks in Example 1 as response versus time using the Evaporative Light Scanning Detector.

FIG. 1 shows the resulting solubility characteristics for three of the reference feedstocks set forth in Table 1 as response versus time using the ELSD. This figure indicates the presence of two distinct features represented by separated peaks. In FIG. 1, the first peak corresponds to the eluted maltenes (heptane solubles) and the last peak corresponds to the eluted asphaltenes.

Figure 2:
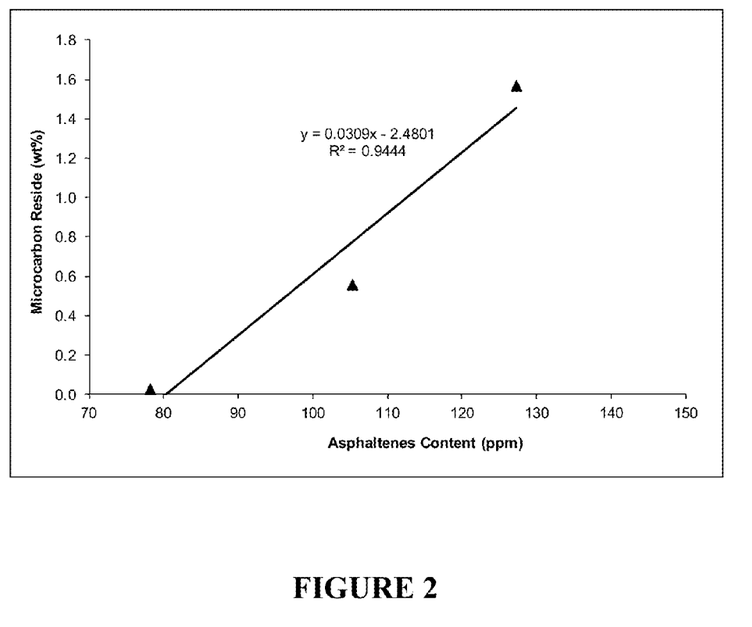
FIG. 2 is a graph showing catalyst life (measured as % of Microcarbon Residue) versus the asphaltenes content determined in Example 1.

As can be seen in FIG. 2, catalyst activity performance, as measured by % of Microcarbon Residue in the feed, can be linearly correlated to the asphaltenes content with a correlation factor of 0.94. This has led to establishment of feed blending guidelines that should not be violated in order to preserve catalyst performance.

TABLE 1

|  | Micro Carbon Residue (wt. %) | Asphaltene Cont. (ppm) |
|---|---|---|
| LVGO | 0.03 | 78.1 |
| HVGO | 0.56 | 105.3 |
| HHVGO | 1.57 | 127.3 |

Example 2

Solutions of three reference feedstocks shown in Table 2 were prepared by dissolving 0.100 g of the feedstocks in 10 mL of methylene chloride. The asphaltene contents of these three samples were determined as described in Example 1 and they are shown in Table 2. Then, the solutions were also injected into the stainless steel column packed with poly (tetrafluoroethylene) (PTFE) using a heptane mobile phase (Solubility Parameter of 15.3 MPa0.5) at a flow rate of 4 mL/min. The maltenes (heptane solubles) eluted from the column as the first peak around 2 minutes after the injection. The mobile phase was then switched in successive steps to solvents of increasing solubility parameters: (1) 10 minutes after the addition of the heptane phase, a blend of 15% dichloromethane/85% n-heptane (Solubility Parameter of 16.05 MPa0.5) was added to the column; (2) 10 minutes after the addition of the blend of 15% dichloromethane/85% n-heptane, a blend of 30% dichloromethane/70% n-heptane (Solubility Parameter of 18.8 MPa0.5) was added to the column; (3) 10 minutes after the addition of the blend of 30% dichloromethane/70% n-heptane, 100% dichloromethane (Solubility Parameter of 20.3 MPa0.5) was added to the column; and (4) 10 minutes after the addition of 100% dichloromethane, a blend of 10% methanol/90% dichloromethane (Solubility Parameter of 21.23 MPa0.5) was added to the column. In this manner, four different asphaltenes solubility fractions were separated with a total analysis time of approximately 50 to 55 minutes.

In this example, the eluted fractions were quantified using Corona Detector (CAD). The analyte eluted from the PTFE column is introduced into the nebulizer, where pressurized nitrogen (40 psi) that has been passed through a carbon filter and a high-efficiency particulate filter is used to form an aerosol of ultra-fine droplets. After evaporation of solvent, the fine particles are measured by an electrometer which in turn generates a signal that is amplified and placed on the detector output. For the case of asphaltenes, the measurement electronic signal, also known as response, represents the solubility characteristics of the asphaltenes present in the sample.

Figure 3:
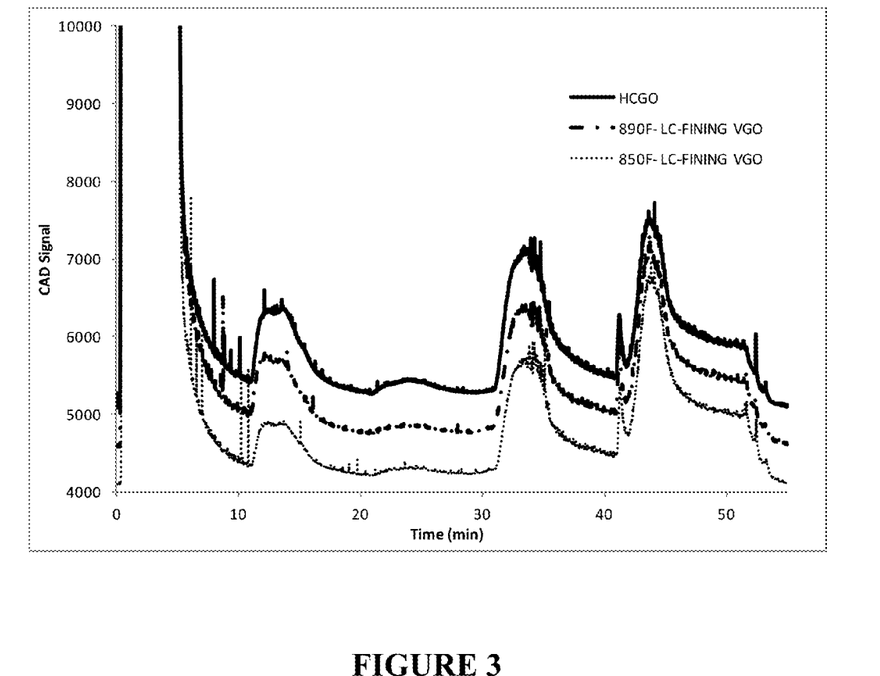
FIG. 3 shows a graph showing the asphaltene solubility fractions for all three feedstocks in Example 2 as response versus time using the Corona Detector (CAD).

FIG. 3 shows the resulting solubility characteristics of the asphaltene solubility fraction distributions for three of the reference feedstocks set forth in Table 2 as response versus time using the CAD. This figure indicates the presence of four distinct features represented by separated peaks. In FIG. 3, the first peak corresponds to the eluted maltenes (heptane solubles) and the last four peaks correspond to each of the eluted asphaltenes from the four different solvent additions. From left to right, the asphaltenes are separated in increasing solubility parameters, i.e., the first peak is considered the least polar asphaltenes and the last peak is considered the most polar asphaltenes. The CAD allows for calculating a percentage of peak area for each of the dissolved asphaltenes.

Figure 4:
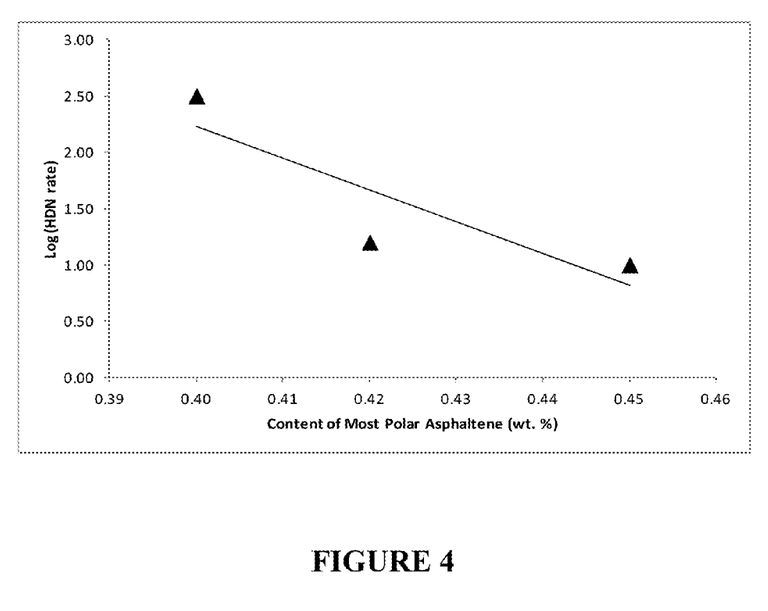
FIG. 4 shows is a graph showing catalyst activity as calculated by the logarithm of the rate of denitrogenation (HDN) versus amount of most polar asphaltenes as determined in Example 2.

FIG. 4 shows the catalyst activity performance of a hydrotreating catalyst as calculated by the logarithm of the rate of denitrogenation (HDN) versus the amount of the most polar asphaltenes. As can be seen, the catalyst performance is inversely proportional to the amount of most polar asphaltenes (solubles in 90/10 Methanol/$CH_2Cl_2$) in the feed.

TABLE 2

|  | Asphaltene Cont. (wt. %) | 15/85 $CH_2Cl_2/C_7$ | 30/70 $CH_2Cl_2/C_7$ | 100% $CH_2Cl_2$ | 90/10 $CH_2Cl_2$/MeOH | Most Polar Asphaltenes (wt. %) |
|---|---|---|---|---|---|---|
| HCGO | 1.2 | 22% | 4% | 41% | 33% | 0.40 |
| 890F- LC-FINING VGO | 1.1 | 19% | 3% | 40% | 38% | 0.42 |
| 850F- LC-FINING VGO | 1.0 | 16% | 2% | 37% | 45% | 0.45 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method comprising the steps of:
   (a) precipitating an amount of polyaromatic compounds from a liquid sample of a first hydrocarbon-containing feedstock having solvated polyaromatic compounds therein with one or more first solvents in a column;
   (b) determining one or more solubility characteristics of the precipitated polyaromatic compounds;
   (c) analyzing the one or more solubility characteristics of the precipitated polyaromatic compounds; and
   (d) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the first hydrocarbon-containing feedstock.

2. The method of claim 1, wherein the polyaromatic compounds are asphaltenes.

3. The method of claim 1, wherein step (b) comprises
   (i) dissolving at least part of the amount of the precipitated polyaromatic compounds in one or more second solvents having a solubility parameter at least about 0.7 $MPa^{0.5}$ higher than the one or more first solvents;
   (ii) dissolving a second amount of the precipitated polyaromatic compounds in one or more third solvents having a solubility parameter higher than the one or more second solvents, wherein the solubility parameter of the one or more third solvents is at least about 21 $MPa^{0.5}$ but no greater than about 30 $MPa^{0.5}$.

4. The method of claim 3, wherein step (c) comprises monitoring the amount of eluted fractions from the column with a liquid chromatography detector which generates a signal proportional to the amount of each eluted fraction.

5. The method of claim 4, comprising calculating a percentage of each peak area for the first amount and the second amount of dissolved polyaromatic compounds from the total peak areas, wherein the peak areas are derived from the signals.

6. The method of claim 3, further comprising prior to step (ii):
dissolving at least part of the amount of the precipitated polyaromatic compounds in one or more fourth solvents having a solubility parameter between the solubility parameter of the second solvent and the solubility parameter of the third solvent; and
dissolving at least part of the amount of the precipitated polyaromatic compounds in one or more fifth solvents having a solubility parameter between the solubility parameter of the fourth solvent and the solubility parameter of the third solvent.

7. The method of claim 1, wherein step (b) comprises:
(i) gradually and continuously changing the one or more first solvents to a first final mobile phase solvent having a solubility parameter at least about 1 $MPa^{0.5}$ higher than the one or more first solvents to dissolve a first amount of the precipitated polyaromatic compounds; and
(ii) gradually and continuously changing the first final mobile phase solvent to a second final mobile phase solvent having a solubility parameter at least about 1 $MPa^{0.5}$ higher than the first final mobile phase solvent to dissolve a second amount of the precipitated polyaromatic compounds.

8. The method of claim 7, wherein step (c) comprises monitoring the concentration of eluted fractions from the column with a liquid chromatography detector.

9. The method of claim 8, comprising calculating a percentage of each peak area for each of the amounts of dissolved polyaromatic compounds from the total peak areas, wherein the peak areas are derived from the signals.

10. The method of claim 5, wherein the measurement of catalyst activity performance comprises one or more measurements in terms of hydrodenitrogenation (HDN) rate, hydrodesulfurization (HDS) rate, hydrodeoxygenation (HDO) rate, hydrogenation rate, hydrodemetallation (HDM) rate, % carbon residue reduction (CRR), % microcarbon residue reduction (MCR), % residue conversion, increase in H/C ratio, reduction of molecular weights, changes in the percentages of Saturates, Aromatics, Resins, and Asphaltenes (SARA) fractions, increase in API or reduction in density, aromatic content, or hydrogen content.

11. The method of claim 10, wherein the mathematical parameter is derived from the peak area obtained for the second amount of dissolved polyaromatic compounds from the one or more third solvents having a solubility parameter of at least about 21 $MPa^{0.5}$ but no greater than about 30 $MPa^{0.5}$.

12. The method of claim 9, wherein the measurement of catalyst activity performance comprises one or more measurements in terms of hydrodenitrogenation (HDN) rate, hydrodesulfurization (HDS) rate, hydrodeoxygenation (HDO) rate, hydrogenation rate, hydrodemetallation (HDM) rate, % carbon residue reduction (CRR), % microcarbon residue reduction (MCR), % residue conversion, increase in H/C ratio, reduction of molecular weights, changes in the percentages of Saturates, Aromatics, Resins, and Asphaltenes (SARA) fractions, increase in API or reduction in density, aromatic content, or hydrogen content.

13. The method of claim 12, wherein the mathematical parameter is derived from the peak area obtained for the second amount of dissolved polyaromatic compounds from the second final mobile phase solvent.

14. The method of claim 1, further comprising the steps of
(e) selecting one or more of the same or different hydrocarbon-containing feedstock samples or products thereof repeating steps (a)-(d); and
(f) comparing the results of the one or more of the same or different hydrocarbon-containing feedstock samples with the results of the first hydrocarbon-containing feedstock sample to predict one or more leading candidate hydrocarbon-containing feedstocks.

15. A method comprising the steps of
(a) selecting one or more hydrocarbon-containing feedstocks, wherein the selection of the one or more hydrocarbon-containing feedstocks comprises:
(i) precipitating an amount of polyaromatic compounds from a liquid sample of a first hydrocarbon-containing feedstock having solvated polyaromatic compounds therein with one or more first solvents in a column;
(ii) determining one or more solubility characteristics of the precipitated polyaromatic compounds;
(iii) analyzing the one or more solubility characteristics of the precipitated polyaromatic compounds; and
(iv) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refinery operation of the first hydrocarbon-containing feedstock; and
(b) feeding the selected hydrocarbon-containing feedstock to one or more crude hydrocarbon refinery components.

16. The method of claim 15, further comprising
(v) selecting one or more second hydrocarbon-containing feedstock samples; repeating steps (i)-(iv); and comparing the results of the one or more second hydrocarbon-containing feedstock samples with the results of the first hydrocarbon-containing feedstock sample to predict one or more leading candidate hydrocarbon-containing feedstocks.

17. The method of claim 15, wherein the one or more crude hydrocarbon refinery components are selected from the group consisting of a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank and a visbreaker.

18. A system comprising:
(a) one or more crude oil hydrocarbon components; and
(b) one or more hydrocarbon-containing feedstocks in fluid communication with the one or more crude hydrocarbon refinery components, wherein the one or more hydrocarbon containing feedstocks are selected by a process comprising:
(i) precipitating an amount of polyaromatic compounds from a liquid sample of a first hydrocarbon-containing feedstock having solvated polyaromatic compounds therein with one or more first solvents in a column;
(ii) determining one or more solubility characteristics of the precipitated polyaromatic compounds;
(iii) analyzing the one Or more solubility characteristics of the precipitated polyaromatic compounds; and
(iv) correlating a measurement of catalyst activity performance for the first hydrocarbon-containing feedstock sample with a mathematical parameter derived from the results of analyzing the one or more solubility characteristics of the precipitated polyaromatic compounds to predict catalyst performance of a catalyst in a refiner operation of the hydrocarbon-containing feedstock.

19. The system of claim 18, wherein the process for selecting one or more hydrocarbon-containing feedstocks further comprises:
   (v) selecting one or more second hydrocarbon-containing feedstock samples; repeating steps (i)-(iv); and comparing the results of the one or more second hydrocarbon-containing feedstock samples with the results of the first hydrocarbon-containing feedstock sample to predict one or more leading candidate hydrocarbon-containing feedstocks.

20. The system of claim 18, wherein the one or more crude hydrocarbon refinery components are selected from the group consisting of a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank and a visbreaker.

* * * * *